(12) United States Patent
Kappus et al.

(10) Patent No.: US 9,113,941 B2
(45) Date of Patent: *Aug. 25, 2015

(54) VESSEL SEALER AND DIVIDER WITH KNIFE LOCKOUT

(71) Applicant: Covidien LP, Mansfield, MA (US)

(72) Inventors: John J. Kappus, Denver, CO (US); Thomas J. Gerhardt, Jr., Littleton, CO (US); Wayne Siebrecht, Golden, CO (US); Larry Johnson, Bennett, CO (US)

(73) Assignee: Covidien LP, Mansfield, MA (US)

( * ) Notice: Subject to any disclaimer, the term of this patent is extended or adjusted under 35 U.S.C. 154(b) by 148 days.

This patent is subject to a terminal disclaimer.

(21) Appl. No.: 13/860,324

(22) Filed: Apr. 10, 2013

(65) Prior Publication Data

US 2013/0231662 A1    Sep. 5, 2013

Related U.S. Application Data

(63) Continuation of application No. 13/550,322, filed on Jul. 16, 2012, now Pat. No. 8,529,566, which is a continuation of application No. 12/548,566, filed on Aug. 27, 2009, now Pat. No. 8,430,876.

(51) Int. Cl.
*A61B 18/12* (2006.01)
*A61B 17/295* (2006.01)
(Continued)

(52) U.S. Cl.
CPC ............ *A61B 17/295* (2013.01); *A61B 18/1445* (2013.01); *A61B 18/1447* (2013.01);
(Continued)

(58) Field of Classification Search
CPC ............... A61B 17/32; A61B 18/1442; A61B 18/1445; A61B 2018/00404; A61B 2018/00601; A61B 2018/0063; A61B 2018/1412; A61B 2018/1445; A61B 2019/304
USPC ...................................................... 606/51–52
See application file for complete search history.

(56) References Cited

U.S. PATENT DOCUMENTS

D249,549 S    9/1978   Pike
D263,020 S    2/1982   Rau, III
(Continued)

FOREIGN PATENT DOCUMENTS

CN    201299462    9/2009
DE    2415263    10/1975
(Continued)

OTHER PUBLICATIONS

U.S. Appl. No. 13/412,879, filed Mar. 6, 2012, David M. Garrison.
(Continued)

*Primary Examiner* — Michael Peffley
*Assistant Examiner* — Daniel Fowler

(57) ABSTRACT

An endoscopic forceps includes a housing having a shaft attached thereto that supports a pair of jaws disposed at a distal end thereof. A drive assembly having a drive shaft with a proximal end is operable to move the jaws relative to one another from an open to closed positions. A knife assembly is operable to advance a knife through tissue disposed between the jaws and includes a flange disposed thereon. A knife lockout is included that has a flange configured to engage the proximal end of the drive shaft and a lockout arm configured to engage the flange of the knife assembly to prevent movement thereof. Movement of the jaws to the closed position causes the proximal end of the drive shaft to engage the flange on the lockout which causes the lockout arm to disengage the flange on the knife assembly to permit advancement of the knife.

10 Claims, 12 Drawing Sheets

(51) Int. Cl.
  *A61B 18/14* (2006.01)
  *A61B 17/32* (2006.01)
  *A61B 18/00* (2006.01)

(52) U.S. Cl.
  CPC ........ *A61B 17/32* (2013.01); *A61B 2018/0063* (2013.01); *A61B 2018/1412* (2013.01); *A61B 2018/1455* (2013.01)

(56) References Cited

U.S. PATENT DOCUMENTS

| | | |
|---|---|---|
| D295,893 S | 5/1988 | Sharkany |
| D295,894 S | 5/1988 | Sharkany |
| D298,353 S | 11/1988 | Manno |
| D299,413 S | 1/1989 | Decarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,597,107 A | 1/1997 | Knodel et al. |
| 5,624,452 A | 4/1997 | Yates |
| D384,413 S | 9/1997 | Zlock et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,762,255 A | 6/1998 | Chrisman et al. |
| H1745 H | 8/1998 | Paraschac |
| 5,807,393 A | 9/1998 | Williamson, IV et al. |
| D402,028 S | 12/1998 | Grimm et al. |
| 5,876,401 A | 3/1999 | Schulze et al. |
| D408,018 S | 4/1999 | McNaughton |
| 5,908,432 A | 6/1999 | Pan |
| D416,089 S | 11/1999 | Barton et al. |
| 6,024,741 A | 2/2000 | Williamson, IV et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,554,829 B2 | 4/2003 | Schulze et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| 7,131,970 B2 | 11/2006 | Moses et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee et al. |
| 7,252,667 B2 | 8/2007 | Moses et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,048,074 B2 | 11/2011 | Masuda |
| 8,070,746 B2 | 12/2011 | Orton et al. |
| 8,070,748 B2 | 12/2011 | Hixson et al. |
| 8,075,558 B2 | 12/2011 | Truckai et al. |
| 8,075,580 B2 | 12/2011 | Makower |
| 8,092,451 B2 | 1/2012 | Schechter et al. |
| 8,114,017 B2 | 2/2012 | Bacher |
| 8,114,122 B2 | 2/2012 | Nau, Jr. |
| 8,123,743 B2 | 2/2012 | Arts et al. |
| 8,128,624 B2 | 3/2012 | Couture et al. |
| 8,133,224 B2 | 3/2012 | Geiselhart |
| 8,133,254 B2 | 3/2012 | Dumbauld et al. |
| 8,142,474 B2 | 3/2012 | Hafner |
| 8,162,940 B2 | 4/2012 | Johnson et al. |
| D661,394 S | 6/2012 | Romero et al. |
| 8,192,433 B2 | 6/2012 | Johnson et al. |
| 8,197,479 B2 | 6/2012 | Olson et al. |
| 8,216,223 B2 | 7/2012 | Wham et al. |
| 8,226,650 B2 | 7/2012 | Kerr |
| 8,241,282 B2 | 8/2012 | Unger et al. |
| 8,241,284 B2 | 8/2012 | Dycus et al. |
| 8,246,618 B2 | 8/2012 | Bucciaglia et al. |
| 8,251,994 B2 | 8/2012 | McKenna et al. |
| 8,298,232 B2 | 10/2012 | Unger |
| 8,303,586 B2 | 11/2012 | Cunningham et al. |
| 8,357,158 B2 | 1/2013 | McKenna et al. |
| 8,357,159 B2 | 1/2013 | Romero |
| 8,394,095 B2 | 3/2013 | Garrison et al. |
| 8,394,096 B2 | 3/2013 | Moses et al. |
| 8,469,716 B2 | 6/2013 | Fedotov |
| 2005/0154387 A1 | 7/2005 | Moses et al. |
| 2006/0074417 A1 | 4/2006 | Cunningham et al. |
| 2007/0078456 A1 | 4/2007 | Dumbauld et al. |
| 2007/0088356 A1 | 4/2007 | Moses et al. |
| 2007/0106297 A1 | 5/2007 | Dumbauld et al. |
| 2008/0033428 A1 | 2/2008 | Artale et al. |
| 2008/0319442 A1 | 12/2008 | Unger et al. |
| 2009/0182327 A1 | 7/2009 | Unger |
| 2012/0109187 A1 | 5/2012 | Gerhardt, Jr. |
| 2012/0118507 A1 | 5/2012 | Brandt |
| 2012/0123402 A1 | 5/2012 | Chernov |
| 2012/0123404 A1 | 5/2012 | Craig |
| 2012/0123410 A1 | 5/2012 | Craig |
| 2012/0123413 A1 | 5/2012 | Chernov |
| 2012/0130367 A1 | 5/2012 | Garrison |
| 2012/0136353 A1 | 5/2012 | Romero |
| 2012/0136354 A1 | 5/2012 | Rupp |
| 2012/0143185 A1 | 6/2012 | Nau, Jr. |
| 2012/0172868 A1 | 7/2012 | Twomey |
| 2012/0172924 A1 | 7/2012 | Allen, IV |
| 2012/0184989 A1 | 7/2012 | Twomey |
| 2012/0184990 A1 | 7/2012 | Twomey |
| 2012/0209263 A1 | 8/2012 | Sharp |
| 2012/0215219 A1 | 8/2012 | Roy |
| 2012/0226275 A1 | 9/2012 | Allen, IV |
| 2012/0239034 A1 | 9/2012 | Horner |
| 2012/0253344 A1 | 10/2012 | Dumbauld |
| 2012/0259331 A1 | 10/2012 | Garrison |
| 2012/0265241 A1 | 10/2012 | Hart |
| 2012/0271346 A1 | 10/2012 | Townsend |
| 2012/0283727 A1 | 11/2012 | Twomey |
| 2012/0283734 A1 | 11/2012 | Ourada |
| 2012/0296205 A1 | 11/2012 | Chernov |
| 2012/0296238 A1 | 11/2012 | Chernov |
| 2012/0296239 A1 | 11/2012 | Chernov |
| 2012/0296317 A1 | 11/2012 | Chernov |
| 2012/0296323 A1 | 11/2012 | Chernov |
| 2012/0296324 A1 | 11/2012 | Chernov |
| 2012/0296332 A1 | 11/2012 | Chernov |
| 2012/0296333 A1 | 11/2012 | Twomey |
| 2012/0296334 A1 | 11/2012 | Kharin |

(56) References Cited

U.S. PATENT DOCUMENTS

| | | | |
|---|---|---|---|
| 2012/0303025 A1 | 11/2012 | Garrison |
| 2012/0316601 A1 | 12/2012 | Twomey |
| 2012/0323238 A1 | 12/2012 | Tyrrell |
| 2012/0330308 A1 | 12/2012 | Joseph |
| 2012/0330309 A1 | 12/2012 | Joseph |
| 2013/0014375 A1 | 1/2013 | Hempstead |
| 2013/0018364 A1 | 1/2013 | Chernov |
| 2013/0018371 A1 | 1/2013 | Twomey |
| 2013/0018372 A1 | 1/2013 | Sims |
| 2013/0018411 A1 | 1/2013 | Collings |
| 2013/0022495 A1 | 1/2013 | Allen, IV |
| 2013/0041370 A1 | 2/2013 | Unger |
| 2013/0041402 A1 | 2/2013 | Chojin |
| 2013/0046295 A1 | 2/2013 | Kerr |
| 2013/0046303 A1 | 2/2013 | Evans |
| 2013/0046306 A1 | 2/2013 | Evans |
| 2013/0046337 A1 | 2/2013 | Evans |
| 2013/0060250 A1 | 3/2013 | Twomey |
| 2013/0066303 A1 | 3/2013 | Hart |
| 2013/0066318 A1 | 3/2013 | Kerr |
| 2013/0071282 A1 | 3/2013 | Fry |
| 2013/0072919 A1 | 3/2013 | Allen, IV |
| 2013/0072927 A1 | 3/2013 | Allen, IV |
| 2013/0079760 A1 | 3/2013 | Twomey |
| 2013/0079762 A1 | 3/2013 | Twomey |
| 2013/0079774 A1 | 3/2013 | Whitney |
| 2013/0082035 A1 | 4/2013 | Allen, IV |
| 2013/0085491 A1 | 4/2013 | Twomey |
| 2013/0085496 A1 | 4/2013 | Unger |
| 2013/0085516 A1 | 4/2013 | Kerr |
| 2013/0103030 A1 | 4/2013 | Garrison |
| 2013/0103031 A1 | 4/2013 | Garrison |
| 2013/0103035 A1 | 4/2013 | Horner |
| 2013/0123837 A1 | 5/2013 | Roy |
| 2013/0138101 A1 | 5/2013 | Kerr |
| 2013/0138102 A1 | 5/2013 | Twomey |
| 2013/0138129 A1 | 5/2013 | Garrison |
| 2013/0144284 A1 | 6/2013 | Behnke, II |
| 2013/0150842 A1 | 6/2013 | Nau, Jr. |
| 2013/0178852 A1 | 7/2013 | Allen, IV |
| 2013/0185922 A1 | 7/2013 | Twomey |
| 2013/0190753 A1 | 7/2013 | Garrison |
| 2013/0190755 A1 | 7/2013 | Deborski |
| 2013/0190760 A1 | 7/2013 | Allen, IV |
| 2013/0197503 A1 | 8/2013 | Orszulak |
| 2013/0218198 A1 | 8/2013 | Larson |
| 2013/0218199 A1 | 8/2013 | Kerr |
| 2013/0219691 A1 | 8/2013 | Reschke |
| 2013/0226226 A1 | 8/2013 | Garrison |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 00931 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 0 509 670 | 10/1992 |
| EP | 1159926 | 12/2001 |
| EP | 1 532 932 | 11/2004 |
| EP | 1 609 430 | 12/2005 |
| EP | 1 632 192 | 3/2006 |
| EP | 1 645 240 | 4/2006 |
| EP | 1 810 625 | 8/2009 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |
| WO | WO 2008/040483 | 4/2008 |

OTHER PUBLICATIONS

U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.

(56) References Cited

OTHER PUBLICATIONS

U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/860,324, filed Apr. 10, 2013, Kappus.
U.S. Appl. No. 13/868,732, filed Apr. 23, 2013, Mueller.
U.S. Appl. No. 13/873,780, filed Apr. 30, 2013, Kerr.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 920, 2000, Thomas P. Ryan.
U.S. Appl. No. 12/336,970, filed Dec. 17, 2008, Paul R. Sremeich.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.

(56) References Cited

OTHER PUBLICATIONS

Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.

(56) References Cited

OTHER PUBLICATIONS

Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

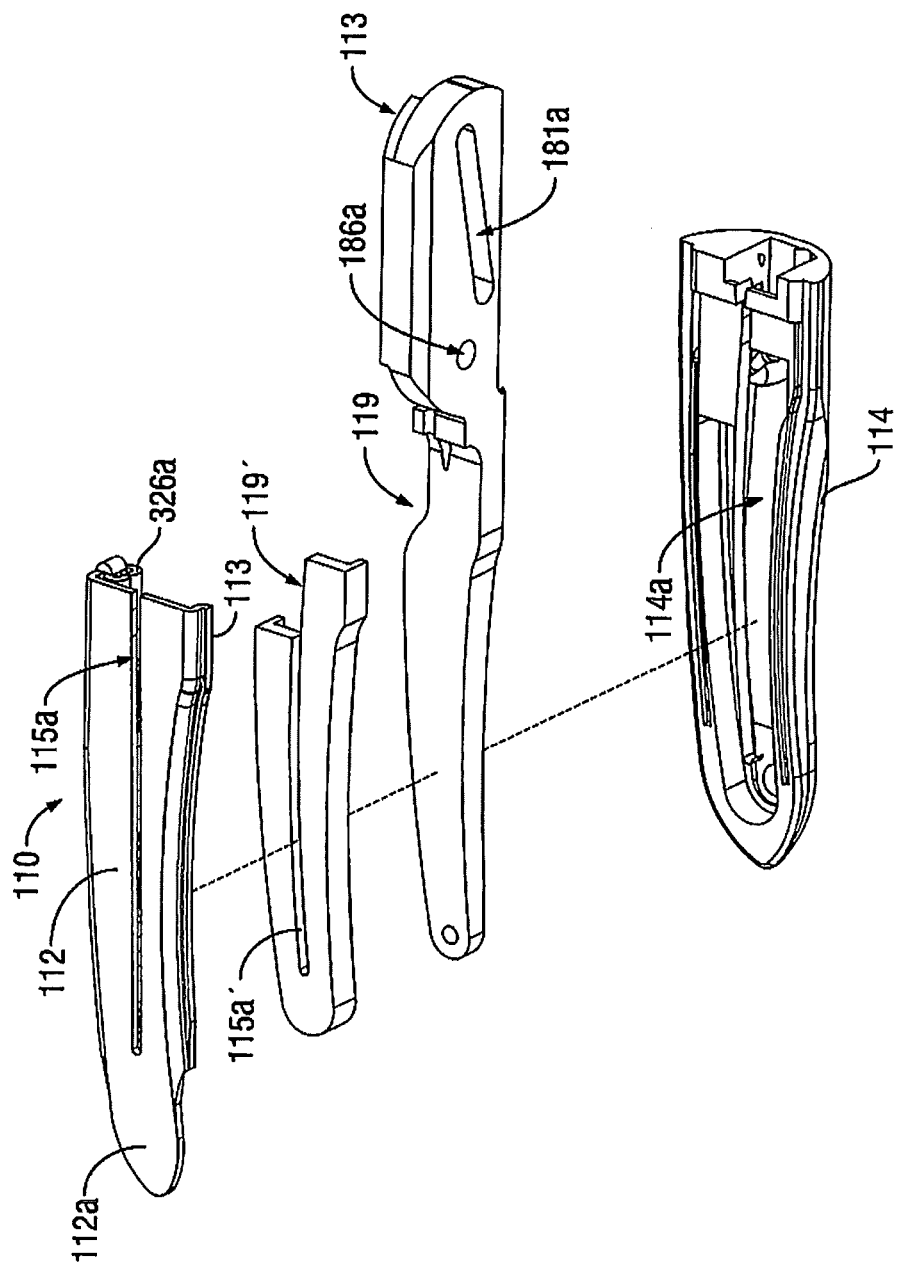

VESSEL SEALER AND DIVIDER WITH KNIFE LOCKOUT

CROSS-REFERENCE TO RELATED APPLICATIONS

This application is a continuation of U.S. patent application Ser. No. 13/550,322, filed on Jul. 16, 2012, now U.S. Pat. No. 8,529,566, which is a continuation of U.S. patent application Ser. No. 12/548,566, filed on Aug. 27, 2009, now U.S. Pat. No. 8,430,876, the entire contents of each of which are incorporated herein by reference.

BACKGROUND

The present disclosure relates to an electrosurgical forceps and, more particularly, the present disclosure relates to an elongated endoscopic combination electrosurgical forceps for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time. As used herein the term, endoscopic is meant to include laparoscopic.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, e.g., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

In order to effectively seal larger vessels (or tissue) two predominant mechanical parameters should be accurately controlled—the pressure applied to the vessel (tissue) and the gap distance between the electrodes or tissue sealing surfaces—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness, which is an indication of a good seal. It has been determined that a typical jaw gap for fusing vessel walls is optimum between 0.001 and 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

It has been found that the pressure range for assuring a consistent and effective seal is between about 3 kg/cm2 to about 16 kg/cm2 and, preferably, within a working range of 7 kg/cm2 to 13 kg/cm2. Manufacturing an instrument that is capable of providing a closure pressure within this working range has been shown to be effective for sealing arteries, tissues and other vascular bundles.

In certain surgical operations, a bipolar forceps is used in combination with a monopolar forceps or monopolar coagulator to treat tissue and control bleeding during the surgery. As such and during the course of a particular operation, a surgeon may be required to substitute a monopolar instrument for the bipolar instrument, which would typically involve substitution through the trocar or cannula. As can be appreciated this may occur on more than one occasion over the course of the operation, which can be quite time consuming and which may unnecessarily subject the instruments to possible non-sterile environments.

Certain surgical instruments have been designed that impede the advancement of the knife or cutting member when the handles are disposed in a closed position to avoid unintended actuation or deployment of the knife through tissue. One such knife lockout design is described in commonly-owned U.S. patent application Ser. No. 11/540,335 entitled IN-LINE VESSEL SEALER AND DIVIDER filed by Dumbauld et al., then entire contents of which is incorporated by reference herein.

SUMMARY

The present disclosure relates to an endoscopic forceps including a housing having a shaft attached thereto which supports a pair of jaw members disposed at a distal end thereof. A drive assembly is included and is disposed in the housing and is operable to move the jaw members relative to one another from an open position wherein the jaw members are disposed in spaced relation relative to one another to a closed position wherein the jaw members cooperate to grasp tissue therebetween. The drive assembly includes a drive shaft having a proximal end. A knife assembly is included and is operable to advance a knife through tissue disposed between the jaw members. The knife assembly includes at least one mechanical interface disposed thereon. A knife lockout is also included having a first mechanical interface configured to operably engage the proximal end of the drive shaft and a second mechanical interface configured to operably engage the mechanical interface of the knife assembly to prevent movement thereof. Movement of the jaw members to the closed position causes the proximal end of the drive shaft to engage the first mechanical interface which, in turn, causes the second mechanical interface to disengage the mechanical interface on the knife assembly to permit selective advancement of the knife. For example, engagement of the first mechanical interface with the proximal end of the drive shaft may cause rotation of the second mechanical interface out of engagement with the mechanical interface of the knife assembly allowing selective actuation of the knife.

In one embodiment, a pair of handles is operatively connected to the drive assembly; the handles are movable relative to the housing to actuate the drive assembly to move the jaw members. In another embodiment, the knife assembly includes a knife shaft that seats within a cap of an elongated knife sleeve supported at a proximal end of the housing. The cap may include a flange that extends therefrom that interfaces with the second mechanical interface of the knife lockout.

In yet another embodiment, the knife lockout may include an adjustment mechanism that precisely aligns the first mechanical interface of the knife lockout with the disposition of proximal end of the drive shaft when the jaw members are in the closed position. The adjustment mechanism may include an eccentric nut that is manually adjustable to align the knife lockout after assembly.

The knife lockout may also include a spring to bias the second mechanical interface of the knife lockout in an engaged position with the mechanical interface of the knife assembly.

The present disclosure also relates to a method of manufacturing a device for dividing vessels or tissue and includes the initial step of: providing a forceps having a housing including a shaft attached thereto that supports a pair of jaw members and at a distal end thereof. A drive assembly is disposed in the housing and is operable to move the jaw members relative to one another from an open position wherein the jaw members and are disposed in spaced relation relative to one another to a closed position wherein the jaw members and cooperate to grasp tissue therebetween. The drive assembly includes a drive shaft having a proximal end. A knife assembly is included and is operable to advance a knife through tissue disposed between the jaw members and. The knife assembly includes a mechanical interface disposed thereon. A knife lockout is included that has a first mechanical interface configured to operably engage the proximal end of the drive shaft and a second mechanical interface configured to operably engage the mechanical interface of the knife assembly and prevent movement thereof.

The method also includes the step of actuating the drive assembly to move the jaw members to the closed position causing the proximal end of the drive shaft to engage the first mechanical interface which, in turn, causes the second mechanical interface to disengage the mechanical interface on the knife assembly and permit selective advancement of the knife.

Another method according to the present disclosure includes a method for separating tissue which includes the steps of: positioning a knife lockout to prevent translation of a knife blade through a knife channel defined between a pair of jaw members; actuating a drive assembly to close the pair of jaw members about tissue and position a proximal end of a drive shaft of the drive assembly to a proximal-most position; and engaging a first mechanical interface extending from the knife lockout with the proximal end of the drive shaft to reposition a second mechanical interface of the knife lockout to allow translation of the knife blade.

BRIEF DESCRIPTION OF THE DRAWINGS

Various embodiments of the subject instrument are described herein with reference to the drawings wherein:

FIG. 4B is a greatly-enlarged, perspective view of the top jaw of the end effector assembly with parts separated;

DETAILED DESCRIPTION

During certain tissue treatment procedures that require transaction of tissue, it may prove useful to employ a knife lockout to prevent unintended advancement of the knife or cutting mechanism through the tissue before the tissue is treated. Moreover, in some instances it may prove useful to prevent translation of the knife when the jaw members are not fully clamped about tissue or are incorrectly clamped about tissue (e.g., too much tissue between jaw members). In this instance, preventing translation of the knife or cutting mechanism will prevent the knife from jamming, miscuing, buckling, pinching or de-railing upon translation or retraction of the knife blade. In some instances, improper deployment or retraction of the knife may render the forceps unusable.

Figure 1A:
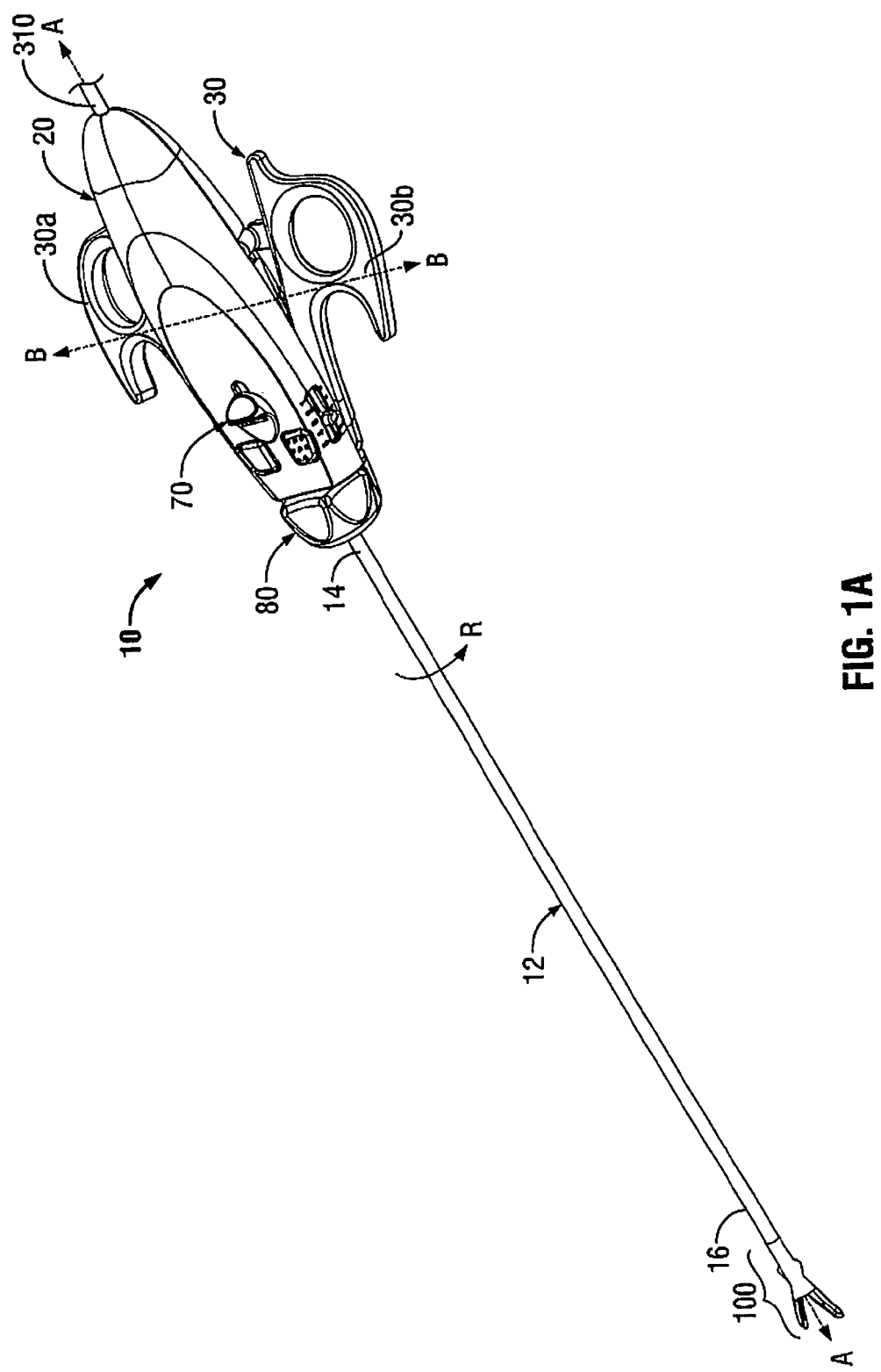
FIG. 1A is a top, perspective view of an endoscopic forceps shown in an open configuration and including a housing, a handle assembly, a shaft and an end effector assembly according to an embodiment of the present disclosure.
Figure 1B:
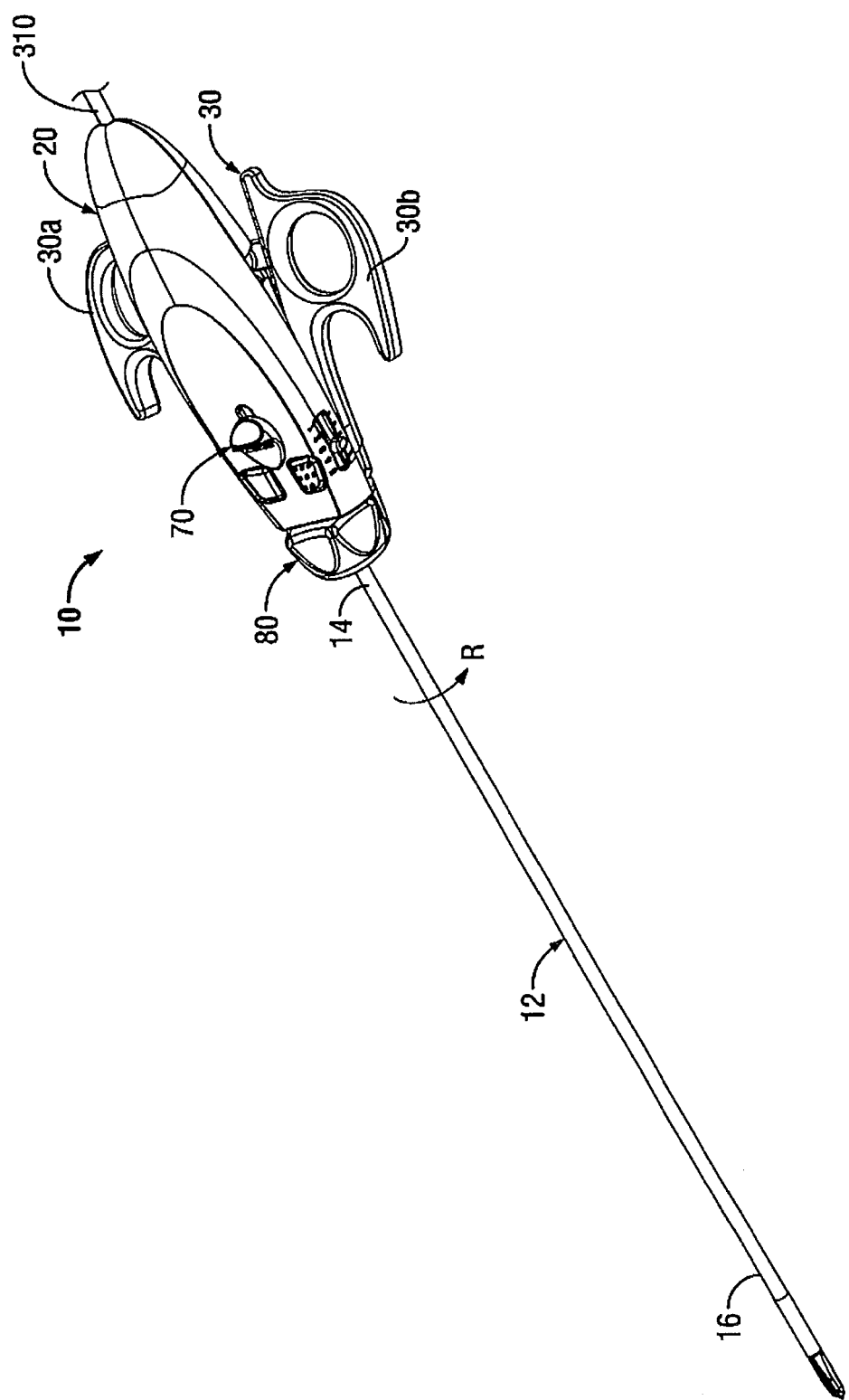
FIG. 1B is a top, perspective view of the endoscopic forceps of FIG. 1A showing the end effector assembly in a closed configuration an embodiment of the present disclosure.

Turning now to FIGS. 1A and 1B, one embodiment of an endoscopic electrosurgical forceps 10 is shown for use with various surgical procedures and generally includes a housing 20, a handle assembly 30, a rotating assembly 80, a knife assembly 70 and an end effector assembly 100 which mutually cooperate to grasp, seal and divide tubular vessels and vascular tissue. Although the majority of the figure drawings depict a forceps 10 for use in connection with endoscopic surgical procedures, the present disclosure may be used for more traditional open surgical procedures.

Forceps 10 includes a shaft 12 which has a distal end 16 dimensioned to mechanically engage the end effector assembly 100 and a proximal end 14 which mechanically engages the housing 20. Details of how the shaft 12 connects to the end effector assembly 100 are described in more detail below. The proximal end 14 of shaft 12 is received within the housing 20 and the connections relating thereto are also described in detail below. In the drawings and in the descriptions which follow, the term "proximal", as is traditional, will refer to the end of the forceps 10 which is closer to the user, while the term "distal" will refer to the end which is further from the user.

Forceps 10 also includes an electrosurgical cable 310 that connects the forceps 10 to a source of electrosurgical energy, e.g., a generator (not shown). Generators such as those sold by Covidien, located in Boulder Colo. may be used as a source of both bipolar electrosurgical energy for sealing vessel and vascular tissues as well as monopolar electrosurgical energy which is typically employed to coagulate or cauterize tissue. It is envisioned that the generator may include various safety and performance features including isolated output, impedance control and/or independent activation of accessories.

Handle assembly 30 includes two movable handles 30a and 30b disposed on opposite sides of housing 20. Handles 30a and 30b are movable relative to one another to actuate the end effector assembly 100 as explained in more detail below with respect to the operation of the forceps 10.

Rotating assembly 80 is mechanically coupled to housing 20 and is rotatable approximately 90 degrees in either direction about a longitudinal axis "A." Rotating assembly 80, when rotated, rotates shaft 12, which, in turn, rotates end effector assembly 100. Such a configuration allows end effector assembly 100 to be rotated approximately 90 degrees in either direction with respect to housing 20.

Figure 4A:
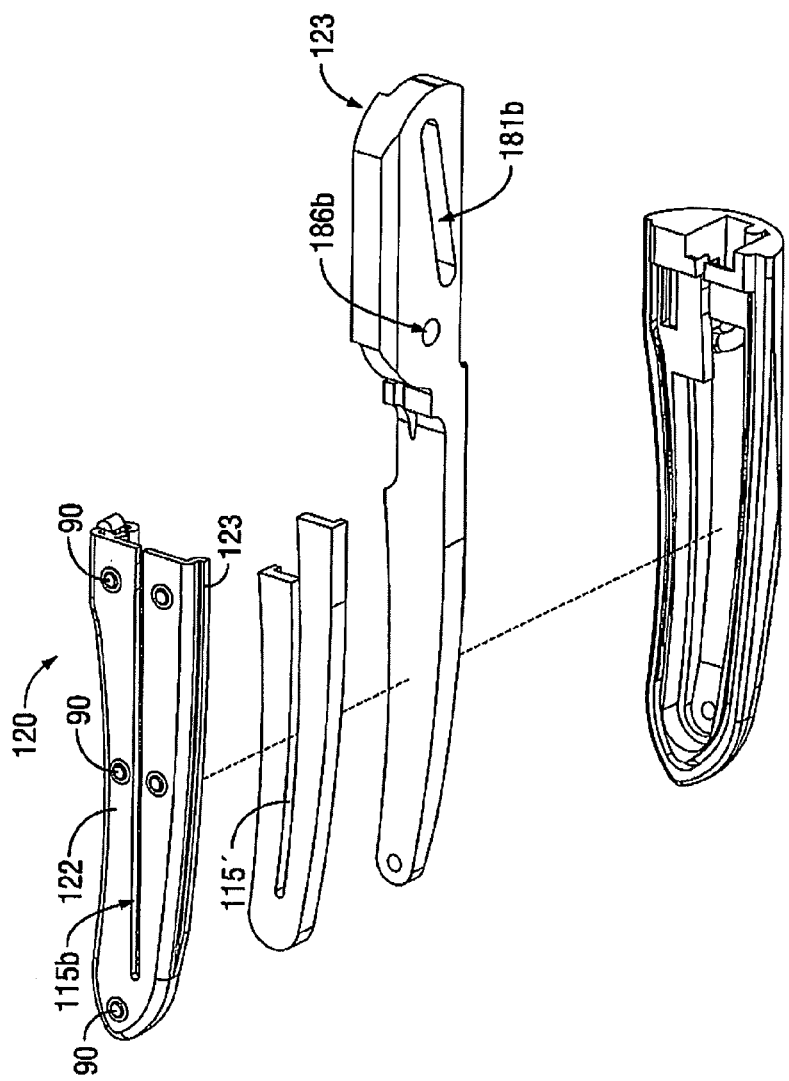
FIG. 4A is a greatly-enlarged, perspective view of the bottom jaw of the end effector assembly with parts separated.

As mentioned above, end effector assembly 100 is attached at the distal end 16 of shaft 12 and includes a pair of opposing jaw members 110 and 120 (see FIGS. 4A and 4B). Handles 30a and 30b of handle assembly 30 ultimately connect to drive assembly 60 (see FIG. 2A) which, together, mechanically cooperate to impart movement of the jaw members 110 and 120 from a first, open position wherein the jaw members 110 and 120 are disposed in spaced relation relative to one another, to a second, clamping or closed position wherein the jaw members 110 and 120 cooperate to grasp tissue therebetween.

Turning now to the more detailed features of the present disclosure as described with respect to FIGS. 1A-5, handles 30a and 30b each include an aperture 33a and 33b, respectively, defined therein which enables a user to grasp and move each respective handle 30a and 30b relative to one another. Handles 30a and 30b also include ergonomically-enhanced gripping elements 39a and 39b, respectively, disposed along an outer edge thereof which are designed to facilitate gripping of the handles 30a and 30b during activation. It is envisioned that gripping elements 39a and 39b may include one or more protuberances, scallops and/or ribs to enhance gripping.

As best illustrated in FIG. 1A, handles 30a and 30b are configured to extend outwardly on opposite sides from a transverse axis "B" defined through housing 20 which is perpendicular to longitudinal axis "A". Handles 30a and 30b are movable relative to one another in a direction parallel to axis "B" to open and close the jaw members 110 and 120 as needed during surgery. Details relating to the inner-working components of forceps 10 are disclosed in commonly-owned U.S. patent application Ser. No. 11/540,335, the entire contents of which being incorporated by reference herein. This forceps style is commonly referred to as an "in-line" or hemostat style forceps. In-line hemostats or forceps are more commonly manufactured for open surgical procedures and typically include a pair of shafts having integrally coupled handles which are movable relative to one another to open and close the jaw members disposed at the distal end thereof.

Figure 2A:
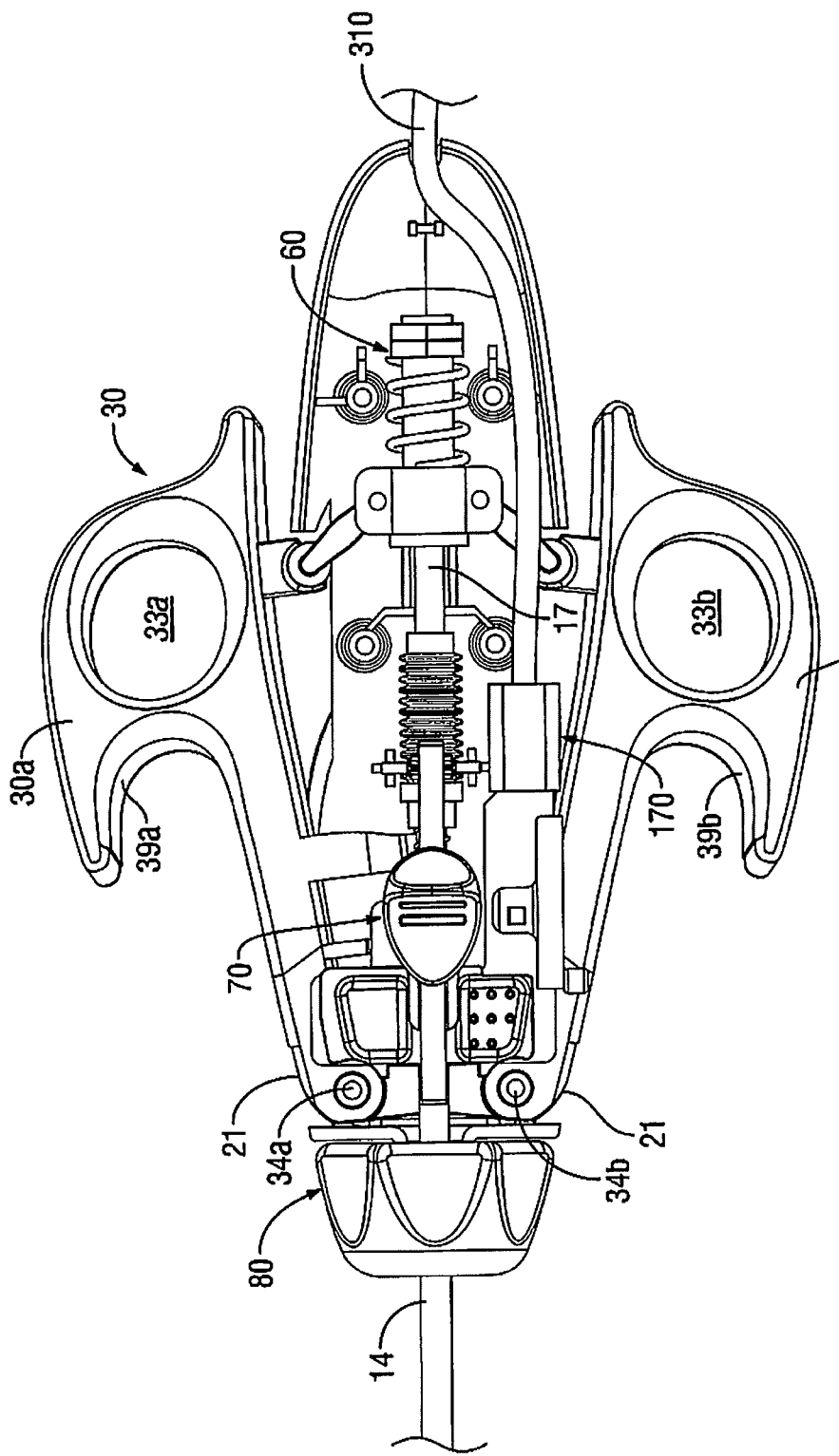
FIG. 2A is an enlarged, top view of the forceps of FIG. 1A showing the disposition of the internal components when the forceps is in an open configuration.
Figure 2B:
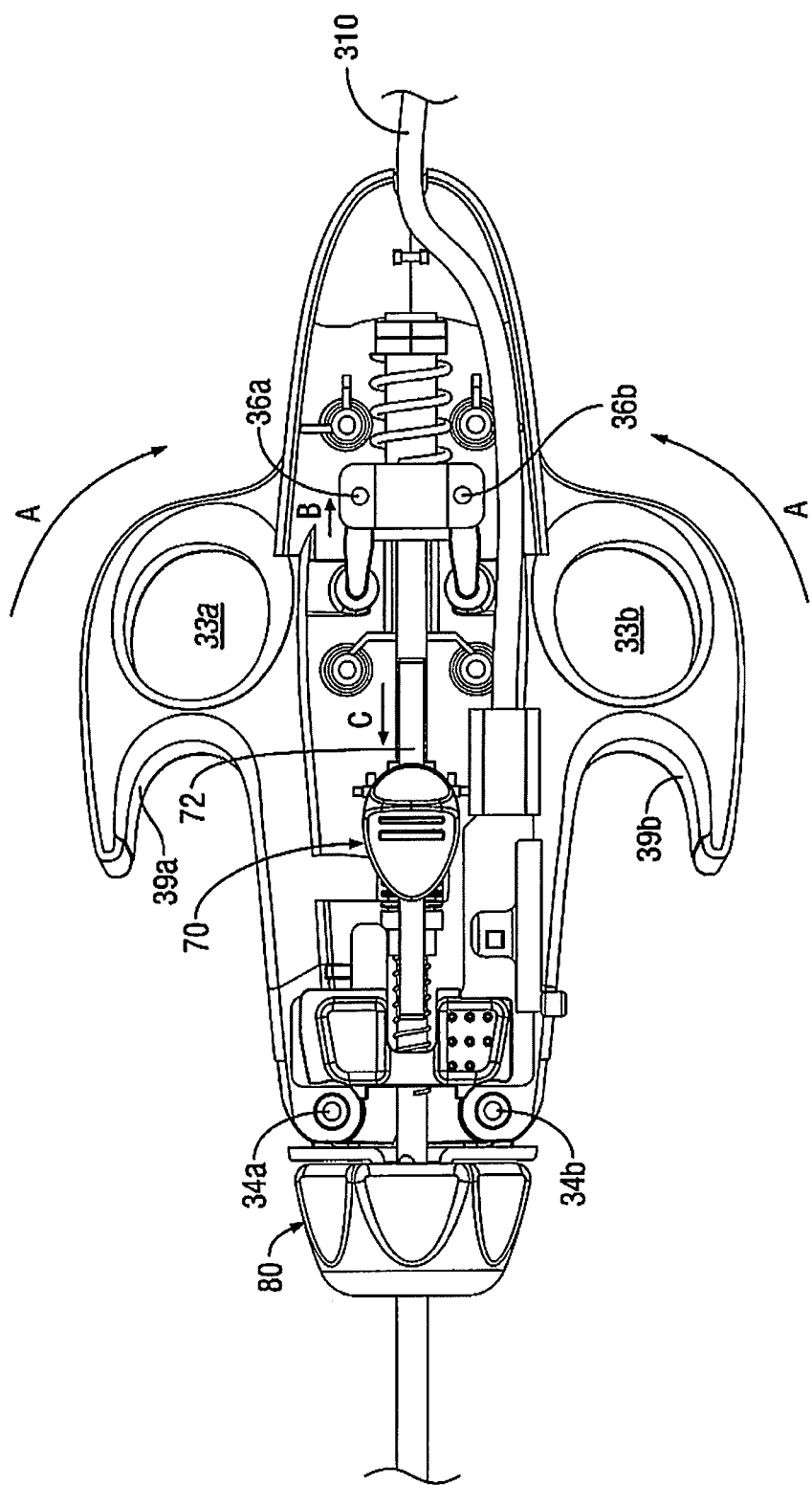
FIG. 2B is an enlarged, top view of the forceps of FIG. 1B showing the disposition of the internal components when the forceps is in a closed configuration.
Figure 3A:
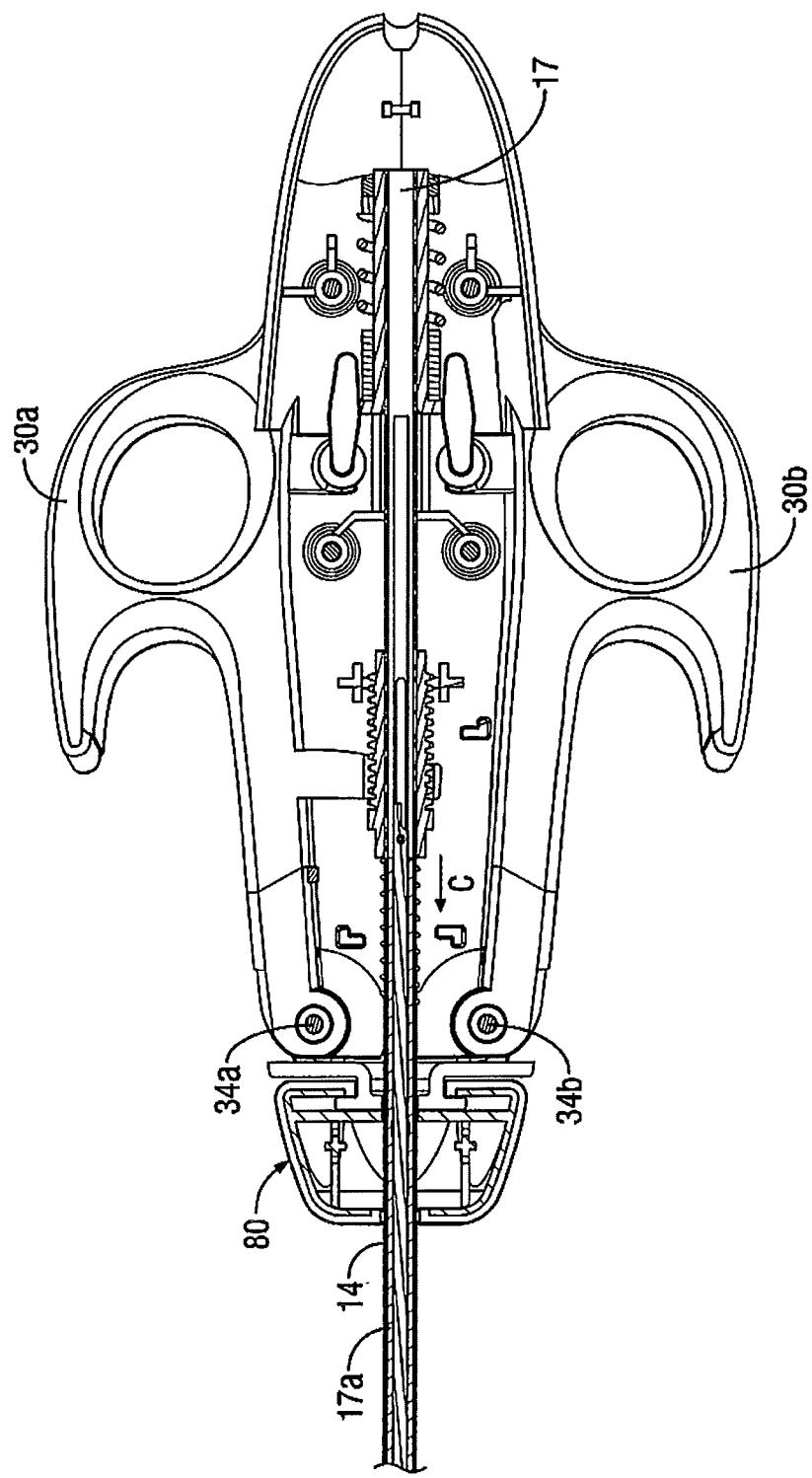
FIG. 3A is an enlarged, top view showing the knife actuator after actuation.
Figure 3B:
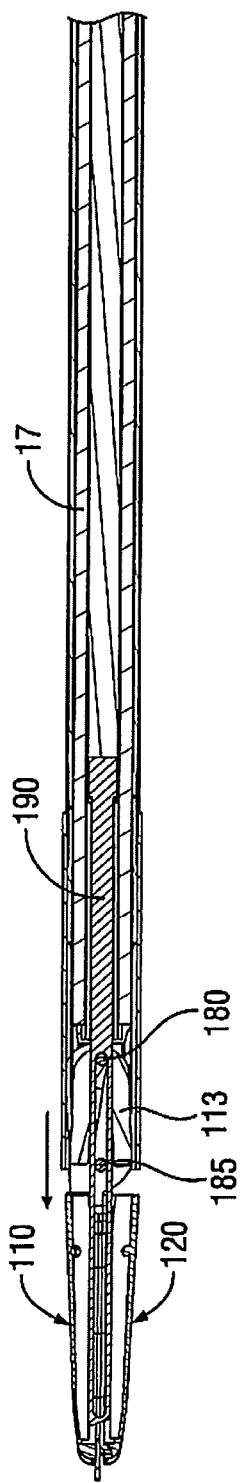
FIG. 3B is a greatly-enlarged, side cross sectional view of the end effector assembly showing the position of the knife after actuation.

As best seen in FIGS. 2A and 2B, the distal end of each handle 30a and 30b is selectively moveable about pivot pins 34a and 34b attached to a distal end 21 of the housing 20 to actuate the jaw members 110 and 120. Movement of the handles 30a and 30b away from one another (and the housing 20) unlocks and opens the handles 30a and 30b and, in turn, the jaw members 110 and 120 for subsequent grasping or re-grasping of tissue. In one embodiment, the handles 30a and 30b may be biased in an open configuration to facilitate handling and manipulation of the jaw members 110 and 120 within an operative field. Various spring-like mechanisms are contemplated which may be utilized to accomplish this purpose.

Movable handles 30a and 30b are designed to provide a distinct lever-like mechanical advantage over conventional handle assemblies. The enhanced mechanical advantage for actuating the jaw members 110 and 120 is gained by virtue of the unique position and combination of several inter-cooperating elements which reduce the overall user forces necessary to obtain and maintain the jaw members 110 and 120 under ideal operating pressures of about 3 kg/cm2 to about 16 kg/cm2. Details relating to the working components the handle assembly and drive assembly are disclosed in above-mentioned U.S. patent application Ser. No. 11/540,335. In other words, it is envisioned that the combination of these elements and their positions relative to one another enables the user to gain lever-like mechanical advantage to actuate the jaw members 110 and 120 enabling the user to close the jaw members 110 and 120 with lesser force while still generating the required forces necessary to effect a proper and effective tissue seal.

Figure 5:
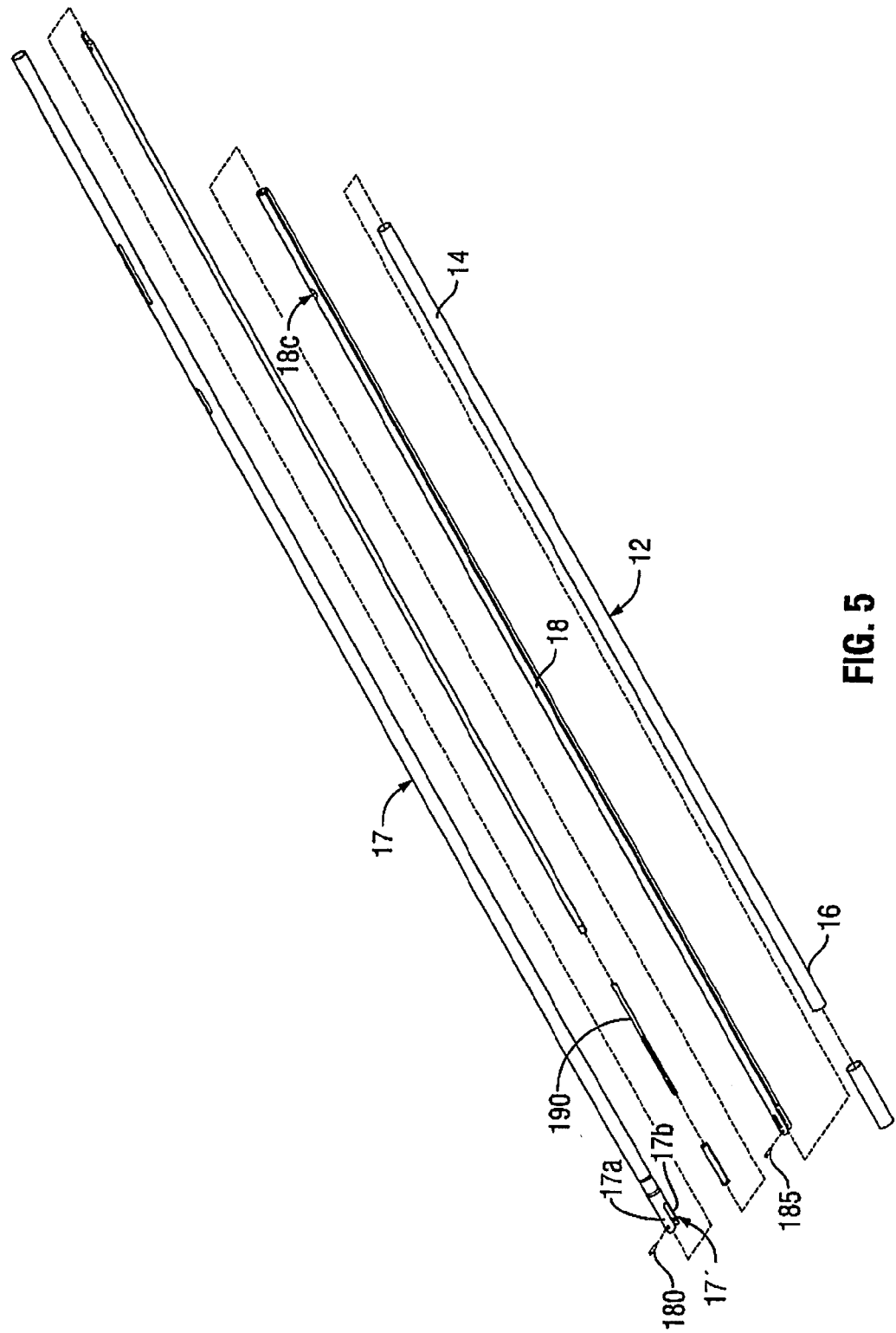
FIG. 5 is a greatly-enlarged, perspective view of the elongated shaft for housing various moving parts of the drive assembly and knife assembly.

As shown in FIGS. 4A, 4B, and 5, the end effector assembly 100 is designed as a bilateral assembly, i.e., both jaw members 110 and 120 pivot relative to one another about a pivot pin 185 disposed therethrough. Each jaw member 110 and 120 includes a corresponding flange 113 and 123 that pivots about a pivot pin 185 disposed between the jaw members 110 and 120 upon translation of a drive rod 180 as explained in more detail below.

More particularly, jaw members 110 and 120 include proximal flanges 113 and 123, respectively, which each include an elongated angled slot 181a and 181b, respectively, defined therethrough. Drive pin 180 mounts jaw members 110 and 120 to the end of a rotating shaft 18 and within a cavity 17' defined at the distal ends 17a and 17b of drive actuator or sleeve 17 (See FIG. 5).

More particularly, upon actuation of the drive assembly 60, the drive sleeve 17 reciprocates which, in turn, causes the drive pin 180 to ride within slots 181a and 181b to open and close the jaw members 110 and 120 as desired. The jaw members 110 and 120, in turn, pivot about pivot pin 185 disposed through respective pivot holes 186a and 186b defined within flanges 113 and 123 of the jaw members 110 and 120. As can be appreciated, squeezing handles 30a and 30b toward the housing 20 pulls drive sleeve 17 and drive pin 180 proximally to close the jaw members 110 and 120 about tissue grasped therebetween and pushing the sleeve 17 distally opens the jaw members 110 and 120 for grasping purposes.

Flanges 113 and 123 of jaw members 110 and 120, respectively, are positioned in an abutting relationship with one another. Flanges 113, 123 are assembled and engaged via pivot pin 185 disposed through apertures 186a, and 186b, respectively. Further, flanges 113 and 123 are pivotable about one another via drive pin 180 disposed through slots 181a and 181b and of flanges 113 and 123, respectively. A knife path may be defined between flanges 113 and 123 that longitudinally aligns with knife channels 115a and 115b defined within jaw members 110 and 120, such that knife blade 190 travels in a substantially straight path through knife channels 115a and 115b defined in jaw members 110 and 120, respectively.

As shown in FIG. 4B, jaw member 110 also includes a support base 119 which extends distally from flange 113 and which is configured to support an insulative plate 119' thereon. Insulative plate 119', in turn, is configured to support an electrically conductive tissue engaging surface or sealing plate 112 thereon. Sealing plate 112 may be affixed atop the insulative plate 119' and support base 119 in any known manner in the art, snap-fit, over-molding, stamping, ultrasonically welded, etc. Support base 119 together with the insulative plate 119' and electrically conductive tissue engaging surface 112 are encapsulated by an outer insulative housing 114. Outer housing 114 includes a cavity 114a that is dimensioned to securely engage the electrically conductive sealing surface 112 as well as the support base 119 and insulative plate 119'. This may be accomplished by stamping, by overmolding, by overmolding a stamped electrically conductive sealing plate and/or by overmolding a metal injection molded seal plate. All of these manufacturing techniques produce jaw member 110 having an electrically conductive surface 112 which is substantially surrounded by an insulating substrate 114.

The electrically conductive surface or sealing plate 112 and the outer housing 114, when assembled, form longitudinally-oriented knife channel 115a defined therethrough for reciprocation of the knife blade 190. It is envisioned that the knife channel 115a cooperates with corresponding knife channel 115b defined in jaw member 120 to facilitate longitudinal extension of the knife blade 190 along a preferred cutting plane to effectively and accurately separate the tissue along the formed tissue seal. As discussed above, when knife blade 190 is deployed, at least a portion of knife blade 190 advances into knife channels 115a and 115b. Handle 30a may include a lockout flange (not shown) which prevents actuation of the knife assembly 70 when the handle 30a is open thus preventing accidental or premature activation of the knife blade 190 through the tissue. A more detailed discussion of the lockout flange is discussed in above-mentioned U.S. patent application Ser. No. 11/540,335.

As explained above and as illustrated in FIGS. 4A and 4B, the knife channel 115 is formed when the jaw members 110 and 120 are closed. In other words, the knife channel 115 includes two knife channel halves—knife channel half 115a disposed in sealing plate 112 of jaw member 110 and knife channel half 115b disposed sealing plate 122 of jaw member 120. Knife channel 115 may be configured as a straight slot with no degree of curvature which, in turn, causes the blade 190 to move through the tissue in a substantially straight fashion. Alternatively and as shown, the knife channel 115 may be curved which has certain surgical advantages.

As mentioned above, when the jaw members 110 and 120 are closed about tissue, knife channels 115a and 115b form a complete knife channel 115 to allow longitudinal extension of the knife blade 190, from the knife path, in a distal fashion to sever tissue along a tissue seal. Knife channel 115 may be completely disposed in one of the two jaw members, e.g., jaw member 120, depending upon a particular purpose. It is also envisioned that jaw member 120 may be assembled in a similar manner as described above with respect to jaw member 110.

Figure 6:
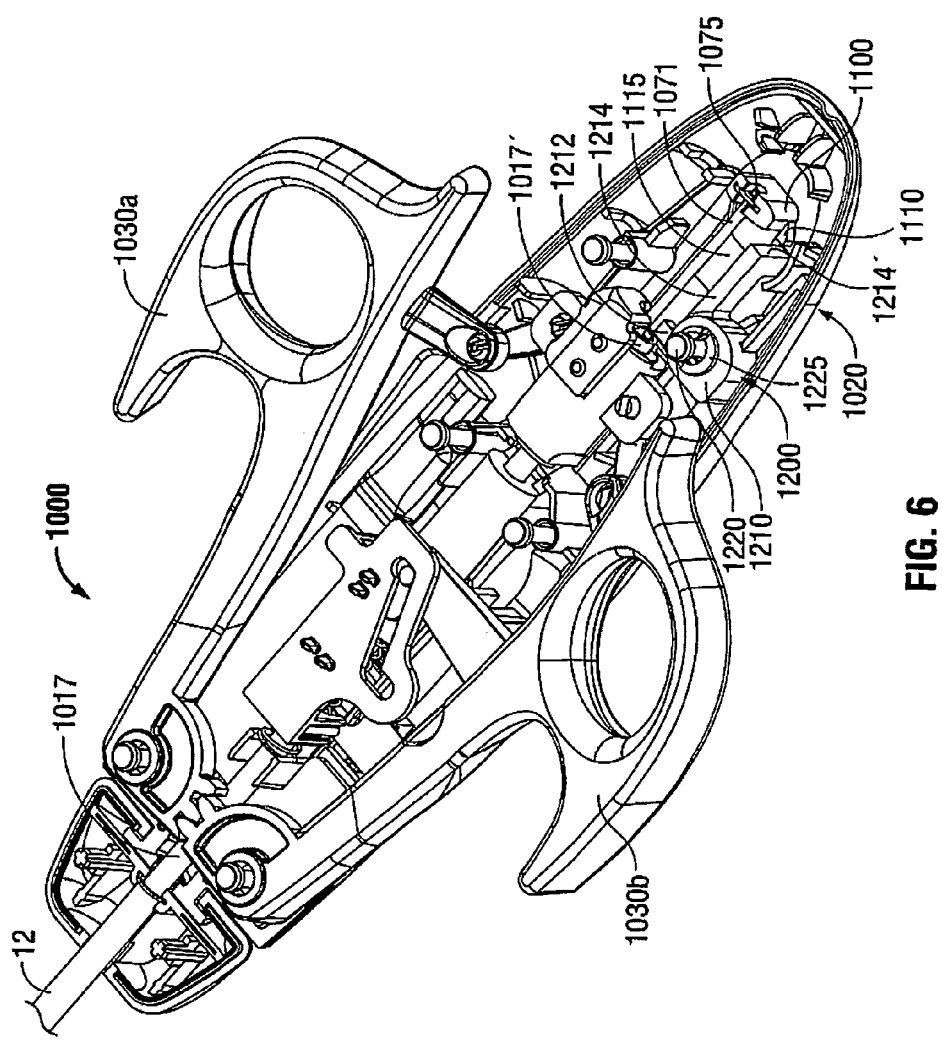
FIG. 6 is an internal view of an alternate embodiment of a forceps according to the present disclosure showing a knife lockout disposed in an engaged position.
Figure 7:
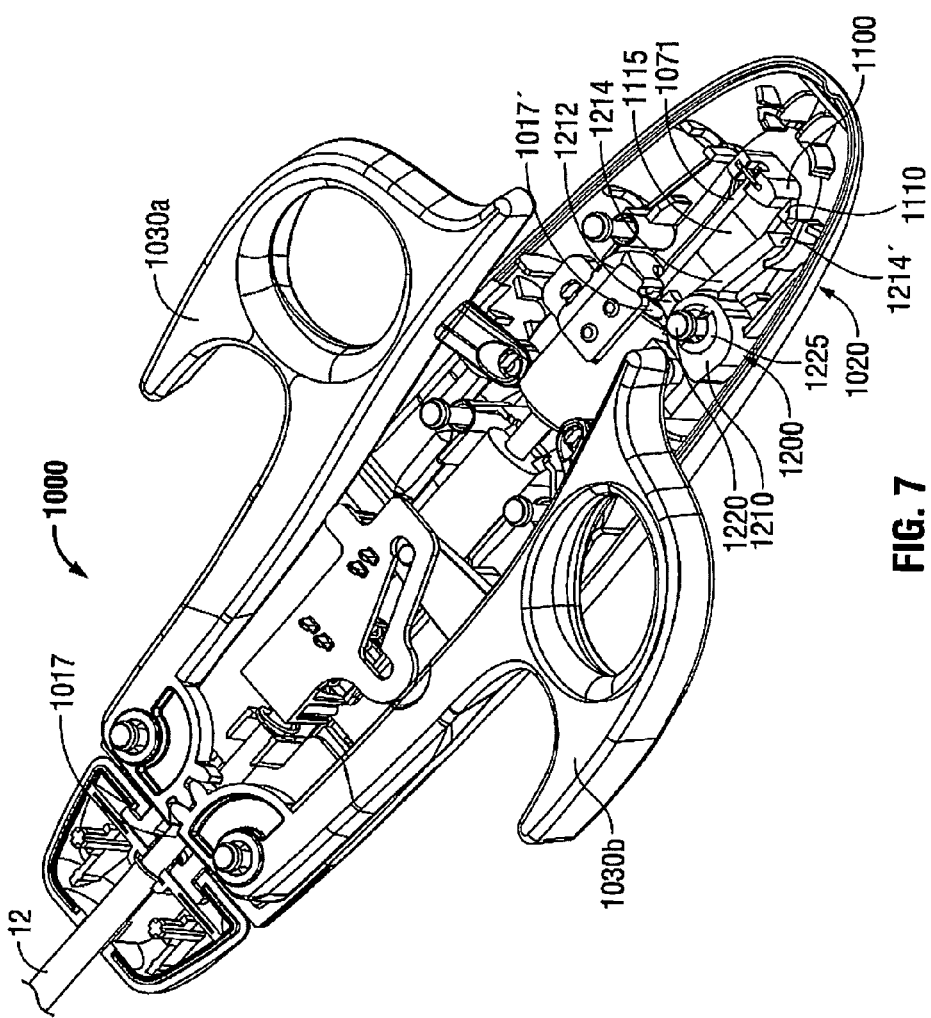
FIG. 7 is an internal view of the embodiment of FIG. 6 showing the knife lockout disposed in a disengaged position by virtue of the movement of the drive shaft.
Figure 8:
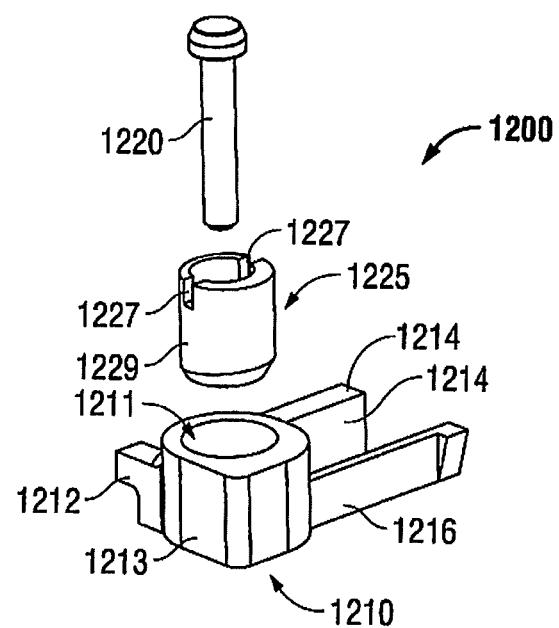
FIG. 8 is an enlarged, exploded view of the knife lockout of FIG. 6.

FIGS. 6-8 show another embodiment of a knife lockout 1200 for use with forceps 10. Unlike the described knife lockout element of commonly-owned U.S. patent application Ser. No. 11/540,335 that prevents advancement of the knife blade 190 when the handles 30a and 30b of forceps 10 are disposed in an open position, lockout 1200 prevents advancement of the knife blade 190 when the jaw members 110 and 120 are disposed in an open position. More particularly, the knife lockout 1200 operably communicates with the drive shaft 1017 such that the position of the drive shaft 1017 (which regulates the opening and closing of the jaw members 110 and 120) dictates a user option for selective advancement of the knife assembly 70. In other words, the disposition of knife lockout 1200 (e.g., "engaged" or "disengaged") is dependent on the position of the drive shaft 1017 and not necessarily the position of the handles 1030a and 1030b. As explained below, the manufacturer can precisely orient an eccentric nut 1225 of the lockout 1200 such that the knife shaft 1071 (and therefore knife blade 190) can only be advanced when the proximal end 1017' of the drive shaft 1017 is fully retracted and the jaw members 110 and 120 are fully closed about tissue.

More particularly, and with respect to FIG. 6, forceps 1000 is similar to the above described forceps 10 with only those exceptions being discussed hereinbelow. Forceps 1000 includes movable handles 1030a and 1030b which together cooperate to actuate the drive assembly (not shown in this embodiment) as discussed above with respect to FIGS. 2A and 2B. In this envisioned embodiment, a proximal end 1017' of the drive shaft 1017 is configured to extend proximally relative to the drive assembly to permit engagement with the knife lockout 1200 (as explained in detail below) when the jaw members 110 and 120 are fully closed about tissue.

As shown in FIGS. 6 and 8, the knife assembly 70 is configured to extend proximally and settle within a proximal end of the housing 1020. The knife shaft 1071 includes a T-shaped proximal end 1075 that seats within a cap 1110 of an elongated knife support sleeve 1115 having a flange 1110 that extends therefrom. Details relating to the interaction of the cap 1100 and the knife lockout 1200 are explained below.

As shown in FIG. 8, knife lockout 1200 includes a lever 1210 that is configured to be supported within the housing 1020 and includes a lockout base 1213 having a lockout arm 1214, a spring arm 1216 and a flange 1212 that extend outwardly therefrom. Flange 1212 is configured to operably engage the proximal end 1017' of drive shaft 1017 when the jaw members 110 and 120 are moved to a fully closed position (See FIG. 7). Upon contact, the flange 1212 is rotated proximally which, in turn, rotates the lockout base 1210 and lockout arm 1214 clockwise such that the proximal end 1214' of the lockout arm 1214 disengages from the flange 1110 of the knife assembly cap 1100. When disengaged, the knife assembly 70 is selectively actuatable by the user to sever tissue disposed between the jaw members 110 and 120. The knife assembly 70 may be spring-biased to return to a fully retracted position upon release thereof.

It is important to note that the knife lockout 1200 is also spring biased such that when the jaw members 110 and 120 are moved from their fully closed position and the proximal end 1017' of the drive shaft 1017 no longer engages the flange 1212, the spring arm 1216 forces the lockout arm 1214 counter-clockwise to reengage the flange 1110 of the knife assembly 70 thereby preventing movement thereof. The spring arm 1216 is biased against the inner periphery of the housing 1020. As can be appreciated, this feature insures that the disposition of the jaw members 110 and 120 and not the disposition of the handles 1030a and 1030b dictates whether the knife assembly 70 may be actuated to separate tissue. In other words, the jaw members must be fully closed in order for the knife 190 to become available for tissue separation.

An adjustment mechanism, e.g., an eccentric adjustment nut 1225, is configured to allow precise alignment of the knife lockout 1200 with the fully retracted position of the proximal end 1017' of the drive shaft 1017. This allows a manufacturer to precisely adjust the relative position of the flange 1212 of the knife lockout 1200 with respect to the position of the proximal end 1017' of the drive shaft 1017 after assembly of the internal components of the forceps 1000 to assure proper disengagement of the knife lockout 1200 when the jaw members 110 and 120 are fully closed. The eccentric adjustment nut 1225 includes a pair of opposing slits 1227 that are configured to facilitate rotation of the nut 1225 which, in turn, precisely aligns the lockout 1200. The eccentric nut 1225 is configured to seat within an aperture defined with the lockout base 1213. A locking bolt 1220 is utilized to lock the nut 1225 in place after alignment of the lockout 1200. Once the housing 1020 is fully assembled, the eccentric adjustment nut 1225 and locking bolt 1220 are secured into place. The locking bolt 1220 may be integrally associated with the housing 20 or may be eliminated and replaced with an alternative boss (not shown).

Other types of alignment mechanisms are also contemplated and include: a living hinge and set screw combination that may be configured to vary the angle of pivot of the lockout 1200; a diagonal slot arrangement that allows precise alignment of the lockout 1200 which is then locked by a set screw; a gear and ratchet alignment device which can be precisely aligned and then locked; a crush feature that locks the lockout device 1200 in an aligned configuration; one or more shims that lock the lockout in precise configuration after alignment; and/or a flexible post and set screw arrangement that aligns and locks the lockout device 1200.

It is contemplated that the above described forceps 100 may be configured in combination with any of the aforementioned features of the forceps 10 described with respect to FIG. 1A-5 or with respect to any of the features described in above-mentioned and commonly-owned U.S. patent application Ser. No. 11/540,335. For example, the forceps 1000 may include a safety lockout, e.g., lockout that prevents activation of one or both switches depending upon the disposition of the jaw members 110 and 120.

A monopolar lockout may also be included that prevents activation of the monopolar switch when the jaw members 110 and 120 are disposed in the open position. The monopolar lockout may include a mechanical interface disposed on one or both of the handles 1030a, 1030b that prevents activation of the monopolar switch when the handles 1030a, 1030b are disposed in an open or first position relative to the housing 1020 and permits activation of the monopolar switch when the handles 1030a, 1030b are disposed in a closed or second position relative to the housing 1020. For example, a pressure activated safety switch (not shown) may be disposed in the housing 1020 and movement of the handles 1030a, 1030b from the open position to the closed position and/or movement of the jaw members from the open to closed position relative to the housing 1020 closes the pressure activated safety switch to allow activation of the monopolar switch.

In another example, the monopolar lockout may include a mechanical interface disposed on one (or both) of the handles 1030a and 1030b that prevents activation of the monopolar switch (or bipolar switch or both switches) when the handles 1030a and 1030b are disposed in a first position relative to the housing 1020 and permits activation of one or both switch when the handles 1030a and 1030b are disposed in a second position relative to the housing.

The present disclosure also relates to a method of manufacturing a device for dividing tissue including the initial step of providing a forceps 1000 having a housing 1020 including a shaft 12 attached thereto that supports a pair of jaw members 110 and 120 at a distal end thereof. A drive assembly 60 is disposed in the housing 1020 and is operable to move the jaw members 110 and 120 relative to one another from an open position wherein the jaw members 110 and 120 are disposed in spaced relation relative to one another to a closed position wherein the jaw members 110 and 120 cooperate to grasp tissue therebetween. The drive assembly 60 includes a drive shaft 1017 having a proximal end 1017'. A knife assembly 70 is included and is operable to advance a knife 190 through tissue disposed between the jaw members 110 and 120. The knife assembly 70 includes a mechanical interface, e.g., flange 1110, disposed thereon. A knife lockout 1200 is included that has a first mechanical interface, e.g., flange 1212, configured to operably engage the proximal end 1017' of the drive shaft 1017 and a second mechanical interface, e.g., lockout arm 1214, configured to operably engage the mechanical interface 1110 of the knife assembly 70 and prevent movement thereof.

The method also includes the step of actuating the drive assembly 60 to move the jaw members 110 and 120 to the closed position causing the proximal end 1017' of the drive shaft 1017 to engage the first mechanical interface 1212 which, in turn, causes the second mechanical interface 1214 to disengage the mechanical interface 1110 on the knife assembly 70 and permit selective advancement of the knife 190.

Another method according to the present disclosure includes a method for separating tissue which includes the steps of: positioning a knife lockout 1200 to prevent translation of a knife blade 190 through a knife channel 115 defined between a pair of jaw members 110 and 120; actuating a drive assembly 60 to close the pair of jaw members 110 and 120 about tissue and position a proximal end 1017' of a drive shaft 1017 of the drive assembly 60 to a proximal-most position; and engaging a first mechanical interface 1212 extending from the knife lockout 1200 with the proximal end 1017' of the drive shaft 1017 to reposition a second mechanical interface 1214 of the knife lockout 1200 to allow translation of the knife blade 190.

From the foregoing and with reference to the various figure drawings, those skilled in the art will appreciate that certain modifications can also be made to the present disclosure without departing from the scope of the same. For example, it may be preferable to add other features to the forceps 10, 1000, e.g., an articulating assembly to axially displace the end effector assembly 100 relative to the elongated shaft 12. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic forceps, comprising:
a housing having a shaft attached thereto, the shaft including a pair of jaw members disposed at a distal end thereof;
a drive assembly operable to move the jaw members relative to one another between an open position wherein the jaw members are disposed in spaced relation relative to one another and a closed position wherein the jaw members cooperate to grasp tissue therebetween, the drive assembly including a drive shaft having a proximal end;
a knife assembly operable to advance a knife through tissue disposed between the jaw members; and
a knife lockout including a first mechanical interface configured to directly contact a proximal-most face of the proximal end of the drive shaft and a second mechanical interface configured to operably engage the knife assembly and prevent movement thereof, wherein movement of the jaw members to the closed position causes the second mechanical interface to disengage the knife assembly.

2. An endoscopic forceps according to claim 1, further comprising a pair of handles operatively connected to the drive assembly and movable relative to the housing to actuate the drive assembly to move the jaw members.

3. An endoscopic forceps according to claim 1, wherein the knife assembly includes a knife shaft that seats within a cap of an elongated knife sleeve supported at a proximal end of the housing, the cap including a flange that extends therefrom that interfaces with the second mechanical interface of the knife lockout.

4. An endoscopic forceps according to claim 1, wherein engagement of said first mechanical interface with the proximal end of the drive shaft causes rotation of the second mechanical interface out of engagement with the knife assembly.

5. An endoscopic forceps according to claim 1, wherein the knife lockout includes a spring operable to bias the second mechanical interface of the knife lockout in an engaged position with the knife assembly.

6. An endoscopic forceps according to claim 1, wherein at least one jaw member is adapted to connect to an electrosurgical energy source for providing electrosurgical energy to tissue disposed between the jaw members.

7. A method of dividing tissue, comprising the steps of:
providing a forceps having:
a housing including a shaft attached thereto, the shaft having a pair of jaw members disposed at a distal end thereof;
a drive assembly operable to move the jaw members relative to one another between an open position wherein the jaw members are disposed in spaced relation relative to one another and a closed position wherein the jaw members cooperate to grasp tissue therebetween, the drive assembly including a drive shaft having a proximal end;
a knife assembly operable to advance a knife through tissue disposed between the jaw members; and
a knife lockout including a first mechanical interface configured to directly contact a proximal-most face of the proximal end of the drive shaft and a second mechanical interface configured to operably engage the knife assembly and prevent movement thereof; and
actuating the drive assembly to move the jaw members to the closed position causing the second mechanical interface to disengage the knife assembly.

8. A method according to claim 7, further comprising the step of biasing the knife lockout to prevent translation of the knife.

9. A method of separating tissue, comprising the steps of:
positioning a knife lockout to prevent translation of a knife through a knife channel defined between a pair of jaw members;
actuating a drive assembly to close the pair of jaw members about tissue and position a proximal end of a drive shaft of the drive assembly to a proximal-most position; and
engaging the knife lockout with a proximal-most face of the proximal end of the drive shaft to reposition the knife lockout to allow translation of the knife.

10. A method according to claim 9, further comprising the step of biasing the knife lockout to prevent translation of the knife.

* * * * *